United States Patent
Stadler et al.

(10) Patent No.: US 9,924,885 B2
(45) Date of Patent: Mar. 27, 2018

(54) RHYTHM DISCRIMINATOR WITH IMMUNITY TO BODY POSTURE

(71) Applicant: MEDTRONIC, INC., Minneapolis, MN (US)

(72) Inventors: Robert W. Stadler, Shoreview, MN (US); Xusheng Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 750 days.

(21) Appl. No.: 14/339,789

(22) Filed: Jul. 24, 2014

(65) Prior Publication Data

US 2016/0022166 A1 Jan. 28, 2016

(51) Int. Cl.
| | |
|---|---|
| A61B 5/0452 | (2006.01) |
| A61N 1/362 | (2006.01) |
| A61B 5/0464 | (2006.01) |
| A61B 5/11 | (2006.01) |
| A61N 1/365 | (2006.01) |

(Continued)

(52) U.S. Cl.
CPC ........ A61B 5/04525 (2013.01); A61B 5/0464 (2013.01); A61B 5/1116 (2013.01); A61N 1/3621 (2013.01); A61N 1/3622 (2013.01); A61N 1/3624 (2013.01); A61N 1/3627 (2013.01); A61N 1/36507 (2013.01); A61N 1/36535 (2013.01); A61N 1/36542 (2013.01); A61N 1/3702 (2013.01); A61B 5/0472 (2013.01); A61B 5/1118 (2013.01); A61B 5/686 (2013.01); A61B 5/7207 (2013.01)

(58) Field of Classification Search
None
See application file for complete search history.

(56) References Cited

U.S. PATENT DOCUMENTS

| | | |
|---|---|---|
| 5,193,535 A | 3/1993 | Bardy et al. |
| 5,342,404 A | 8/1994 | Alt et al. |

(Continued)

FOREIGN PATENT DOCUMENTS

| | | |
|---|---|---|
| AU | 2010201351 A1 | 4/2010 |
| AU | 2012265575 A1 | 1/2013 |

(Continued)

OTHER PUBLICATIONS

Zhang, "A Beat-Morphology Matching Scheme for Cardiac Sensing and Event Detection", U.S. Appl. No. 13/826,097, filed Mar. 14, 2013, 37 pages.

(Continued)

*Primary Examiner* — Brian T Gedeon

(57) ABSTRACT

An implantable medical device system includes an implantable cardioverter defibrillator (ICD) for detecting and treating ventricular tachycardia (VT). The ICD includes a sensing module for sensing a cardiac signal from available cardiac signal sensing vectors. A control module generates morphology templates of the cardiac signals for multiple patient postures for each of the available sensing vectors and determines a set of posture-independent template features. An unknown cardiac rhythm is classified in response to comparing features of a cardiac signal received during the unknown rhythm to the set of posture-independent features.

10 Claims, 6 Drawing Sheets

(51) Int. Cl.
*A61N 1/37* (2006.01)
*A61B 5/00* (2006.01)
*A61B 5/0472* (2006.01)

(56) References Cited

U.S. PATENT DOCUMENTS

| | | | |
|---|---|---|---|
| 5,354,316 | A | 10/1994 | Keimel |
| 5,447,519 | A | 9/1995 | Peterson |
| 5,545,186 | A | 8/1996 | Olson et al. |
| 5,593,431 | A | 1/1997 | Sheldon |
| 5,865,760 | A | 2/1999 | Lidman et al. |
| 6,044,297 | A | 3/2000 | Sheldon et al. |
| 6,104,949 | A | 8/2000 | Pitts Crick et al. |
| 6,393,316 | B1 | 5/2002 | Gillberg et al. |
| 6,397,100 | B2 | 5/2002 | Stadler et al. |
| 6,745,068 | B2 | 6/2004 | Koyrakh et al. |
| 6,975,904 | B1 | 12/2005 | Sloman |
| 7,031,771 | B2 | 4/2006 | Brown et al. |
| 7,336,999 | B1 | 2/2008 | Koh |
| 7,496,409 | B2 | 2/2009 | Greenhut et al. |
| 7,706,869 | B2 | 4/2010 | Cao et al. |
| 7,894,894 | B2 | 2/2011 | Stadler et al. |
| 7,904,153 | B2 | 3/2011 | Greenhut et al. |
| 7,941,214 | B2 | 5/2011 | Kleckner et al. |
| 7,991,471 | B2 | 8/2011 | Ghanem et al. |
| 7,996,070 | B2 * | 8/2011 | van Dam ........... A61B 5/04525 600/483 |
| 8,050,751 | B2 | 11/2011 | Zhang et al. |
| 8,068,901 | B2 | 11/2011 | Ghanem et al. |
| 8,160,684 | B2 | 4/2012 | Ghanem et al. |
| 8,301,233 | B2 | 10/2012 | Zhang et al. |
| 8,321,016 | B2 | 11/2012 | Holmstrom et al. |
| 8,332,022 | B2 | 12/2012 | Brown et al. |
| 8,380,295 | B2 | 2/2013 | Greenhut et al. |
| 8,391,944 | B2 | 3/2013 | O'Brien et al. |
| 8,428,697 | B2 | 4/2013 | Zhang et al. |
| 8,428,718 | B2 | 4/2013 | Stadler et al. |
| 8,428,720 | B2 | 4/2013 | Corbucci et al. |
| 8,435,185 | B2 | 5/2013 | Ghanem et al. |
| 8,437,842 | B2 | 5/2013 | Zhang et al. |
| 8,868,165 | B1 | 10/2014 | Nabutovsky et al. |
| 9,486,637 | B2 * | 11/2016 | Greenhut ............ A61B 5/0464 |
| 2002/0091331 | A1 | 7/2002 | Onoda et al. |
| 2003/0097153 | A1 | 5/2003 | Bardy et al. |
| 2006/0111643 | A1 | 5/2006 | Cazares et al. |
| 2007/0156057 | A1 | 7/2007 | Cho et al. |
| 2008/0132965 | A1 | 6/2008 | Ostroff et al. |
| 2008/0188901 | A1 | 8/2008 | Sanghera et al. |
| 2009/0054796 | A1 | 2/2009 | Sanghera et al. |
| 2009/0054938 | A1 | 2/2009 | Ostroff et al. |
| 2009/0228057 | A1 | 9/2009 | Allavatam et al. |
| 2010/0274148 | A1 | 10/2010 | Zhang et al. |
| 2010/0331903 | A1 | 12/2010 | Zhang et al. |
| 2010/0331904 | A1 | 12/2010 | Warren et al. |
| 2011/0098775 | A1 | 4/2011 | Allavatam et al. |
| 2012/0089032 | A1 | 4/2012 | Park et al. |
| 2012/0101392 | A1 | 4/2012 | Bhunia et al. |

FOREIGN PATENT DOCUMENTS

| | | |
|---|---|---|
| AU | 2013267073 A1 | 1/2014 |
| EP | 2025363 A2 | 2/2009 |
| WO | 2004105871 A1 | 12/2004 |
| WO | 2006039693 A1 | 4/2006 |
| WO | 2008153450 A1 | 12/2008 |
| WO | 2009131976 A1 | 10/2009 |

OTHER PUBLICATIONS (PCT/US2015/036572) PCT Notification of Transmittal of the International Search Report and the Written Opinion of the International Searching Authority, dated Sep. 18, 2015, 11 pages.

* cited by examiner

RHYTHM DISCRIMINATOR WITH IMMUNITY TO BODY POSTURE

TECHNICAL FIELD

The disclosure relates generally to implantable medical devices and, in particular, to a method and apparatus for discriminating supraventricular tachycardia (SVT) from ventricular tachycardia (VT) when cardiac signal morphology changes with patient body posture.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical leads may be configured to allow electrodes or other sensors to be positioned at desired locations for delivery of electrical stimulation or sensing of physiological conditions. For example, electrodes or sensors may be carried at a distal portion of a lead. A proximal portion of the lead may be coupled to an implantable medical device housing, which may contain circuitry such as signal generation circuitry and/or sensing circuitry.

Some IMDs, such as cardiac pacemakers or implantable cardioverter defibrillators (ICDs), provide therapeutic electrical stimulation to or monitor the heart of the patient via electrodes carried by one or more implantable leads. The leads may be transvenous, i.e., implanted in the heart through one or more veins, sometimes referred to as endocardial leads. Other leads may be non-transvenous leads implanted outside the heart. In either case, the electrical stimulation provided by the IMD may include signals such as pacing pulses, cardioversion shocks or defibrillation shocks to address abnormal cardiac rhythms such as bradycardia, tachycardia or fibrillation.

In some cases, the IMD senses signals representative of intrinsic depolarizations of the heart and analyzes the sensed signals to identify normal or abnormal rhythms. Upon detection of an abnormal rhythm, the device may deliver an appropriate electrical stimulation signal or signals to restore or maintain a more normal rhythm. For example, an IMD may deliver pacing pulses to the heart upon detecting tachycardia or bradycardia, and deliver cardioversion or defibrillation shocks to the heart upon detecting tachycardia or fibrillation.

SUMMARY

In general, the disclosure is directed to techniques for discriminating between treatable heart rhythms, e.g., ventricular tachycardia (VT), and non-treatable heart rhythms, e.g., supra-ventricular tachycardia (SVT), of a heart of a patient. An ICD operating in accordance with the techniques performs a morphology analysis for detecting and discriminating VT and SVT based on posture-independent cardiac signal template features.

To reduce the likelihood of misclassification of the rhythm, the ICD generates and stores cardiac electrical signal templates for multiple patient body postures for all available cardiac signal sensing vectors. For each sensing vector the ICD extracts posture-independent features from the templates. In one example, the ICD compares analogous features of a cardiac electrical signal sensed during an unknown rhythm to at least a portion of the stored features. The ICD classifies the unknown rhythm as VT or SVT based on the comparison.

In one example, the disclosure provides a method comprising sensing a first cardiac signal during a known cardiac rhythm from each of a plurality of available sensing vectors; for each of the available sensing vectors, generating a plurality of morphology templates of the first cardiac signal for each of a plurality of patient postures; determining a set of template features from each of the plurality of morphology templates; for each of the plurality of available sensing vectors, comparing the set of template features from one of the plurality of morphology templates corresponding to one of the plurality of postures to each of the sets of template features from all of the other morphology templates corresponding to all of the other of the plurality of postures; for each of the plurality of available sensing vectors, storing a set of posture-independent template features in response to the comparing; sensing a second cardiac signal during an unknown cardiac rhythm from at least one of the plurality of available sensing vectors; determining features from the second cardiac signal that are analogous to the set of posture-independent template features stored for the at least one of the plurality of available sensing vectors; comparing the features determined from the second cardiac signal to the analogous set of posture-independent template features; and classifying the unknown cardiac rhythm in response to comparing the features determined from the second cardiac signal to the analogous set of posture-independent template features.

In another example, the disclosure provides an implantable medical device (IMD) comprising a sensing module coupled to a plurality of electrodes defining a plurality of available sensing vectors and a control module coupled to the sensing module. The control module is configured to sense a first cardiac signal during a known cardiac rhythm from each of the plurality of available sensing vectors and, for each of the plurality of available sensing vectors, generate a plurality of morphology templates of the first cardiac signal for each of a plurality of patient postures and determine a set of template features from each of the plurality of morphology templates. For each of the plurality of available sensing vectors, the control module is further configured to compare the set of template features from one of the plurality of morphology templates corresponding to one of the plurality of postures to each of the sets of template features from all of the other morphology templates corresponding to all of the other of the plurality of postures and store a set of posture-independent template features in response to the comparing. The control module senses a second cardiac signal during an unknown cardiac rhythm from at least one of the plurality of available sensing vectors, determines features from the second cardiac signal that are analogous to the set of posture-independent template features stored for the at least one of the plurality of available sensing vectors, compares the features determined from the second cardiac signal to the analogous set of posture-independent template features; and classifies the unknown cardiac rhythm in response to comparing the features determined from the second cardiac signal to the analogous set of posture-independent template features.

In another example, the disclosure provides a computer-readable storage medium comprising instructions which, when executed by a control module in an implantable medical device, cause the implantable medical device to sense a first cardiac signal during a known cardiac rhythm from each of the plurality of available sensing vectors; for each of the plurality of available sensing vectors, generate a plurality of morphology templates of the first cardiac signal for each of a plurality of patient postures; determine a set of template features from each of the plurality of morphology templates; for each of the plurality of available sensing vectors, compare the set of template features from one of the plurality of morphology templates corresponding to one of the plurality of postures to each of the sets of template features from all of the other morphology templates corresponding to all of the other of the plurality of postures; for each of the plurality of available sensing vectors, store a set of posture-independent template features in response to the comparing; sense a second cardiac signal during an unknown cardiac rhythm from at least one of the plurality of available sensing vectors; determine features from the second cardiac signal that are analogous to the set of posture-independent template features stored for the at least one of the plurality of available sensing vectors; compare the features determined from the second cardiac signal to the analogous set of posture-independent template features; and classify the unknown cardiac rhythm in response to comparing the features determined from the second cardiac signal to the analogous set of posture-independent template features.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1:
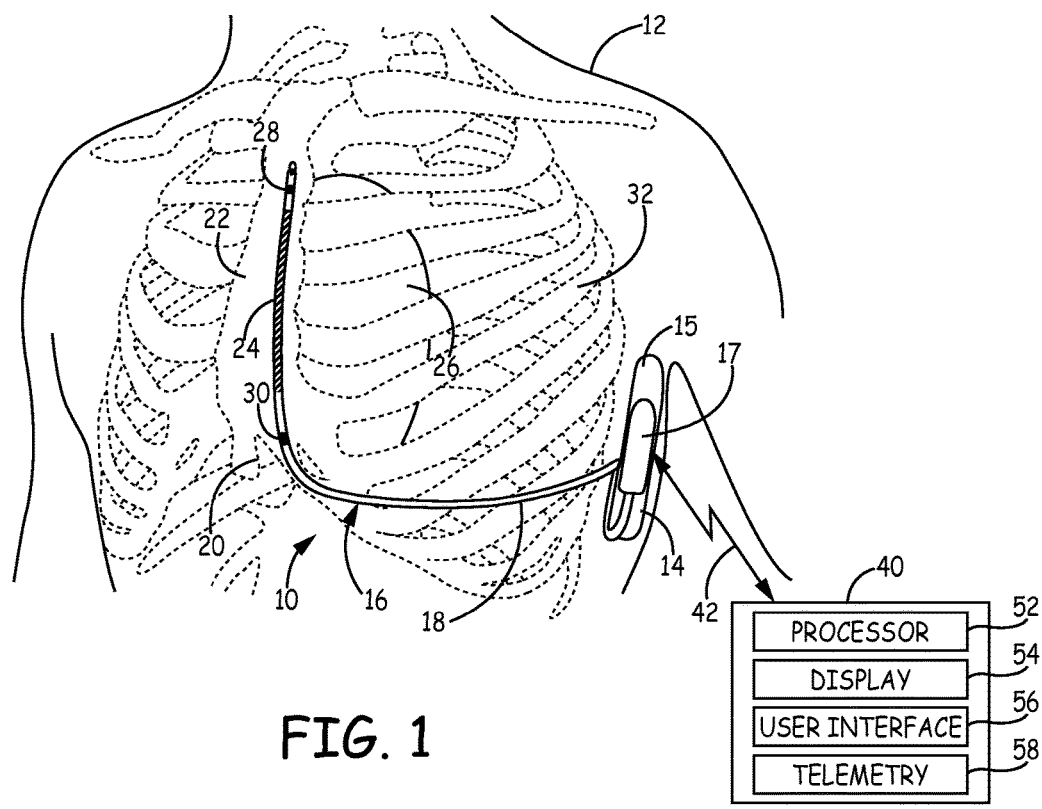
FIG. 1 is a conceptual diagram of a patient implanted with an example IMD system that includes an ICD coupled to a subcutaneous defibrillation lead.

In general, this disclosure describes techniques for distinguishing between treatable arrhythmias and non-treatable arrhythmias. Treatable arrhythmias refer to abnormal heart rhythms for which stimulation therapy is delivered to one or both of the ventricles. Treatable arrhythmias may include ventricular tachycardia (VT) or ventricular fibrillation (VF). Treatable arrhythmias generally pose an immediate danger to the patient and therapy is needed in order to ensure the safety of the patient. Non-treatable arrhythmias, on the other hand, refer to abnormal heart rhythms that typically do not require stimulation therapy to be delivered to either of the ventricles. Non-treatable arrhythmias may include supraventricular tachycardia (SVT), which includes sinus tachycardia, atrial tachycardia (AT), atrial fibrillation (AF), atrial flutter, atrioventricular nodal reentrant tachycardia (AVNRT), atrioventricular reciprocating tachycardia (AVRT), or the like. Non-treatable arrhythmias do not generally pose an immediate danger to the patient. As such, non-treatable arrhythmias may go untreated, i.e., no stimulation therapy is delivered to the heart. In other instances, non-treatable arrhythmias may be treated using stimulation therapy, but the stimulation therapy is not delivered to the ventricles of the patient.

Accurately determining whether the heart rhythm is treatable or non-treatable prevents inadvertent delivery of therapy to a ventricle of the patient when no therapy to the ventricle is necessary (e.g., in the case of a rhythm mischaracterized as a treatable arrhythmia) or withholding stimulation therapy when the therapy to the ventricle is necessary (e.g., in the case of a rhythm mischaracterized as a non-treatable arrhythmia). Unnecessary delivery of stimulation therapy to the patient may be uncomfortable for the patient, needlessly depletes the power source of the medical device and, in some patients or circumstances, can induce more dangerous arrhythmias.

Some ICD systems rely on electrodes that are implanted outside the heart for receiving electrocardiogram (ECG) signals that are used to detect and discriminate heart rhythms. These ICD systems may be desirable for some patients because the elimination of transvenous leads eliminates the need to advance catheters and leads into the blood vessels and heart of the patient and reduces the risk of serious infection by eliminating the pathway for infection from a subcutaneous pocket to the patient's heart. The ECG is sensed from electrodes implanted outside the cardiovascular system, for example subcutaneously, submuscularly, or substernally, in some examples. The ECG obtained from electrodes implanted outside the cardiovascular system may be subject to morphology changes due to changes in patient posture.

An ICD according to the present disclosure includes a tachyarrhythmia detector for discriminating between VT and SVT using ECG morphology analysis. The ECG is sensed from electrodes implanted outside the cardiovascular system, for example subcutaneously, submuscularly or substernally. The ECG obtained from electrodes implanted outside the cardiovascular system may be subject to morphology changes due to changes in patient posture. The tachyarrhythmia detector is configured to analyze the ECG acquired during different patient postures to generate a set of ECG signal features that are substantially insensitive to changes in patient posture but highly discriminative for detecting VT and SVT. The tachyarrhythmia detector performs a comparative morphology analysis that utilizes the ECG features previously identified as being substantially immune to patient posture changes but reliable for discriminating between VT and SVT.

FIG. 1 is a conceptual diagram of a patient 12 implanted with an example IMD system 10 that includes an ICD 14 coupled to a defibrillation lead 16. Defibrillation lead 16 includes a proximal end that is connected to ICD 14 and a distal end that includes one or more electrodes. Defibrillation lead 16 is illustrated in FIG. 1 as being implanted subcutaneously, e.g., in tissue and/or muscle between the skin and the ribcage 32 and/or sternum 22. Defibrillation lead 16 extends subcutaneously from ICD 14 toward xiphoid process 20. At a location near xiphoid process 20 defibrillation lead 16 bends or turns and extends subcutaneously superior, substantially parallel to sternum 22. Although illustrated as being offset laterally from and extending substantially parallel to sternum 22 in the example of FIG. 1, defibrillation lead 16 may be implanted over sternum 22, offset from sternum 22, but not parallel to sternum 22 (e.g., angled laterally from sternum 22 at either the proximal or distal end).

Figure 2:
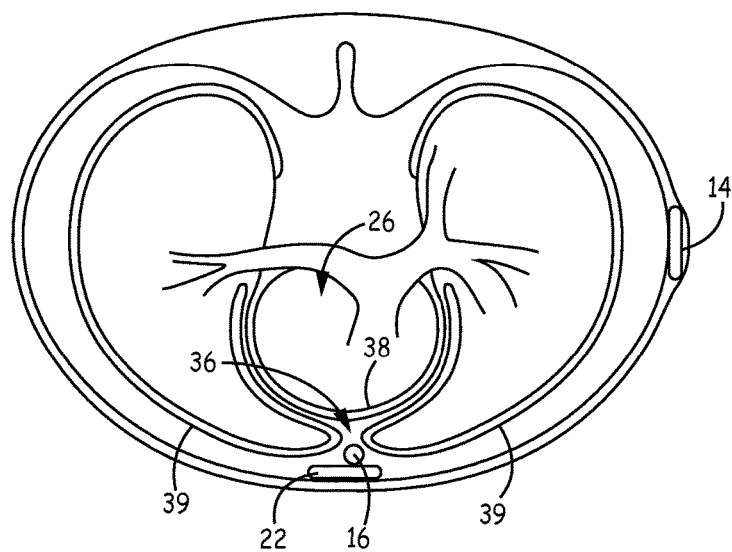
FIG. 2 is a transverse view of the patient in FIG. 1 depicting the defibrillation lead implanted in an alternate location.

In other instances, lead 16 may be implanted at other extravascular locations. As shown in a transverse view of patient 12 in FIG. 2, lead 16 may be implanted at least partially in a substernal location, e.g., between the ribcage 32 and/or sternum 22 and heart 26. In one such configuration, a proximal portion of lead 16 extends subcutaneously from ICD 14 toward sternum 22 (not seen in the transverse view of FIG. 2) and a distal portion of lead 16 extends superior under or below the sternum 22 in the anterior mediastinum 36. Anterior mediastinum 36 is bounded laterally by pleurae 39, posteriorly by pericardium 38, and anteriorly by sternum 22.

In some instances, the anterior wall of anterior mediastinum 36 may also be formed by the transversus thoracis and one or more costal cartilages. Anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 16 extends along the posterior side of sternum 22 substantially within the loose connective tissue and/or substernal musculature of anterior mediastinum 36. Lead 16 may be at least partially implanted in other intrathoracic locations, e.g., other non-vascular, extra-pericardial locations, including the gap, tissue, or other anatomical features around the perimeter of and adjacent to, but not attached to, the pericardium or other portion of heart 26 and not above sternum 22 or ribcage 32.

In another example, ICD 14 may be implanted subcutaneously outside the ribcage 32 in an anterior medial location. Lead 16 may be tunneled subcutaneously into a location adjacent to a portion of the latissimus dorsi muscle of patient 12, from a medial implant pocket of ICD 14 laterally and posteriorly to the patient's back to a location opposite heart 26 such that the heart 26 is generally disposed between the ICD 14 and distal electrode coil 24 and distal sensing electrode 28.

Referring again to FIG. 1, defibrillation lead 16 includes an elongated lead body 18 carrying electrodes 24, 28 and 30 located along the distal portion of the length of the lead body 18. Lead body 18 insulates one or more elongated electrical conductors (not illustrated) that extend from a respective electrode 24, 28 and 30 through the lead body to a proximal connector (not shown) that is coupled to ICD 14. Lead body 16 may be formed from a non-conductive material, such as silicone, polyurethane, fluoropolymers, or mixtures thereof or other appropriate materials, and is shaped to form one or more lumens within which the one or more conductors extend. The conductors are electrically coupled to ICD circuitry, such as a therapy module or a sensing module, via connections in an ICD connector assembly 17 that includes a connector bore for receiving the proximal connector of lead 16 and associated electrical feedthroughs crossing ICD housing 15. The electrical conductors transmit therapy from a therapy module within ICD 14 to one or more of electrodes 24, 28, and 30, and transmit sensed electrical signals from one or more of electrodes 24, 28, and 30 to the sensing module within ICD 14.

Defibrillation lead 16 is shown in FIG. 1 to include a defibrillation electrode 24, which may be an elongated coil electrode, along the distal portion of defibrillation lead 16. Defibrillation lead 16 is located on lead 16 such that when ICD system 10 is implanted a therapy vector between defibrillation electrode 24 and a housing or can electrode 15 of ICD 14 is substantially through or across the ventricle(s) of heart 26.

Defibrillation lead 16 also includes one or more sensing electrodes 28 and 30, located toward the distal portion of defibrillation lead 16. In the example illustrated in FIG. 1, sensing electrodes 28 and 30 are separated from one another by defibrillation electrode 24. In other words, sensing electrode 28 is located distal to defibrillation electrode 24 and sensing electrode 30 is proximal to defibrillation electrode 24. ICD system 10 may sense electrical activity of heart 26 via one or more of sensing vectors that include combinations of electrodes 28 and 30 and the housing or can electrode 15 of ICD 14. For example, ICD 14 may receive a subcutaneous ECG signal across a sensing vector between electrodes 28 and 30, a sensing vector between electrode 28 and the conductive housing or can electrode 15, a sensing vector between electrode 30 and the conductive housing or can electrode 15, or any combination of electrodes 28, 30 and the housing or can electrode 15. In some instances, ICD 14 may even sense cardiac electrical signals using a sensing vector that includes defibrillation electrode 24.

ICD 14 receives cardiac electrical signals from one or more of the sensing vectors described above for detecting tachyarrhythmias. ICD 14 may deliver one or more cardioversion or defibrillation shocks via defibrillation electrode 24 in response to detecting VT or VF. ICD 14 may also provide pacing therapy, such as anti-tachycardia pacing (ATP) and/or post-shock pacing after a cardioversion or defibrillation shock when pacing capabilities are available.

ICD 14 includes a housing 15, also referred to herein as housing electrode or can electrode 15, which forms a hermetic seal that protects internal electronic components of ICD 14. The housing 15 may be formed of a conductive material, such as titanium, titanium alloy, or other conductive material, to serve as an electrode. Housing 15 may function as a "can electrode" since the conductive housing or a portion thereof may be coupled to internal circuitry to be used as an indifferent or ground electrode during sensing or defibrillation shock delivery.

ICD 14 also includes connector assembly 17 (also referred to as a connector block or header) that includes electrical feedthroughs through which electrical connections are made between electrical conductors within lead 16 and electronic components included within the housing 15. As will be described in further detail herein, housing 15 may enclose one or more processors, memory devices, transmitters, receivers, sensors, sensing circuitry, therapy circuitry and other appropriate components.

The example shown in FIG. 1 is illustrative in nature and should not be considered limiting of the techniques described in this disclosure. In other examples, ICD 14 and one or more associated leads may be implanted at other locations. For example, ICD 14 may be implanted in a subcutaneous pocket in the right chest. In this example, defibrillation lead 16 may extend subcutaneously from the device toward the manubrium of the sternum 22 and bend or turn and extend subcutaneously or substernally inferiorly from the manubrium of the sternum, substantially parallel with the sternum.

The techniques disclosed herein may be implemented in numerous ICD and electrode configurations that include one or more housing-based electrodes and/or one or more lead-based electrodes for enabling sensing of an ECG signal across one or more sensing vectors and for delivering electrical stimulation therapies to heart 26. The IMD system 10 is an extravascular IMD system because lead 16 is positioned in an extravascular location outside the blood vessels, heart 26 and pericardium 38. It is understood that while ICD 14 and lead 16 may be positioned between the skin and a muscle layer of the patient 12, ICD 14 and any associated leads could be positioned in any extravascular location of the patient, such as below a muscle layer or even within the thoracic cavity.

An external device 40 is shown in telemetric communication with ICD 14 by a communication link 42. External device 40 may include a processor 52, display 54, user interface 56 and telemetry unit 58. Processor 52 controls external device operations and processes data and signals received from ICD 14. Display 54, which may include a graphical user interface, displays data and other information to a user for reviewing ICD operation and programmed parameters as well as ECG signals retrieved from ICD 14. User interface 56 may include a mouse, touch screen, key pad or the like to enable a user to interact with external device 40 to initiate a telemetry session with ICD 14 for retrieving data from and/or transmitting data to ICD 14. Telemetry unit 58 is configured for bidirectional communication with a telemetry module included in ICD 14 and is configured to operate in conjunction with processor 52 for sending and receiving data relating to ICD functions via communication link 42.

Communication link 42 may be established between ICD 14 and external device 40 using a radio frequency (RF) link such as Bluetooth, Wi-Fi, or Medical Implant Communication Service (MICS) or other RF bandwidth. External device 40 may be embodied as a programmer used in a hospital, clinic or physician's office to retrieve data from ICD 14 and to program operating parameters and algorithms in ICD 14 for controlling ICD 14 functions. For example, external device 40 may be used to program ICD tachyarrhythmia detection parameters, such as VT and VF interval zones, VT and VF NID, and detection thresholds relating to morphology analysis of the ECG signals. External device 40 may also be used to program therapy control parameters, such as the shock energy used to terminate VT or VF. External device 40 may alternatively be embodied as a home monitor or handheld device.

The tachycardia discrimination and therapy delivery techniques disclosed herein are useful in an extravascular IMD system such as the system 10 shown in FIG. 1 that may be susceptible to posture-induced ECG morphology changes. Sensing electrodes 28 and 30 carried by lead 16 and located in subcutaneous or substernal locations may be more susceptible to posture-induced changes in the cardiac signal morphology than sensing electrodes attached to or within the heart. An extravascular IMD system is less invasive and may be more easily implanted than a system including transvenous or epicardial leads. However, techniques disclosed herein may be implemented in other examples of IMD systems that include transvenous intracardiac leads and electrodes, epicardial electrodes or other lead and electrode systems. Examples of other IMD systems in which the techniques disclosed herein could be implemented for discriminating VT from SVT in the presence of posture-induced cardiac signal morphology changes are generally disclosed in U.S. Pat. No. 7,031,771 (Brown et al.) and U.S. Pat. No. 5,447,519 (Peterson), and U.S. Pat. No. 7,496,409 (Greenhut, et al.) all of which patents are incorporated herein by reference in their entirety.

Figure 3:
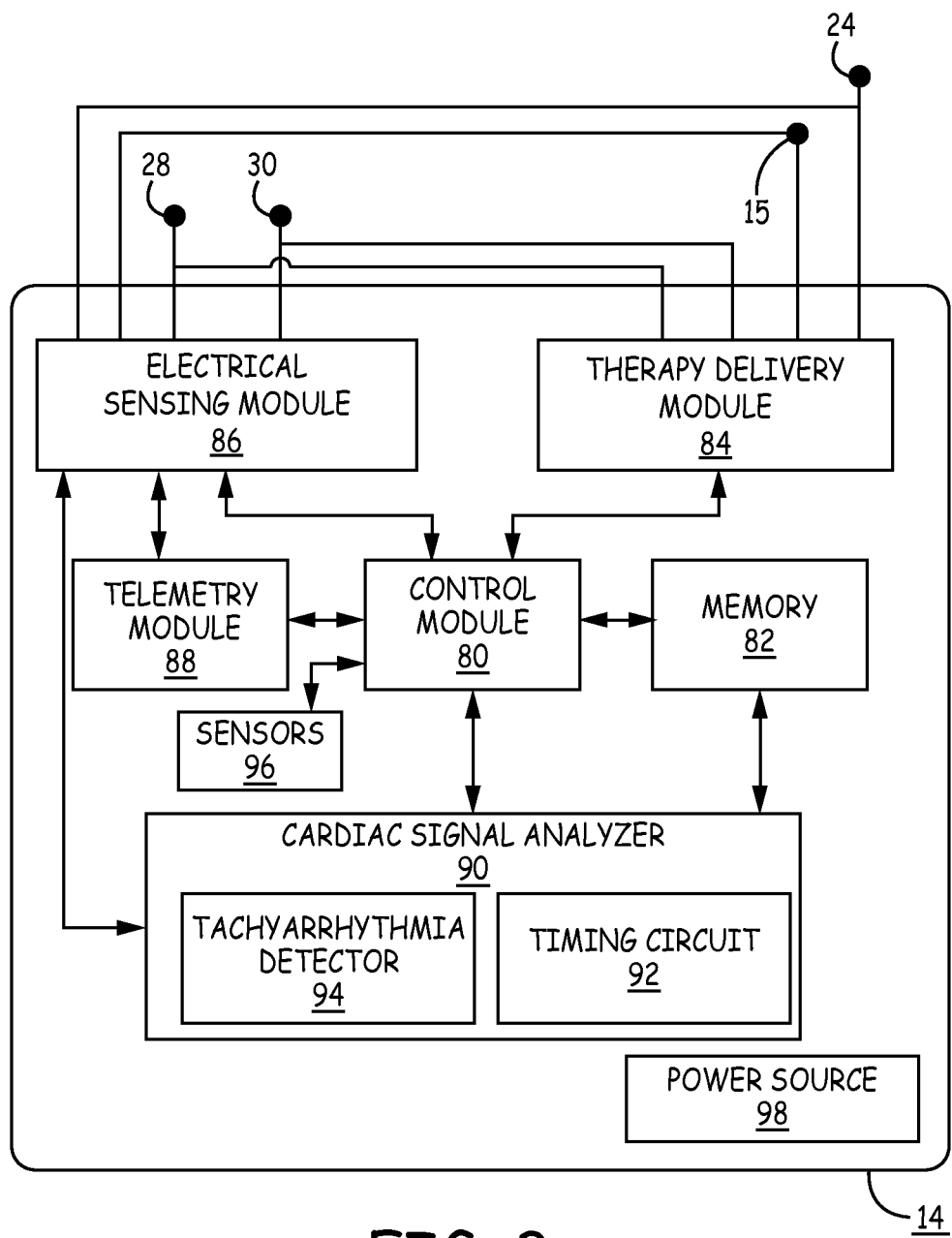
FIG. 3 is a schematic diagram of an ICD according to one embodiment.

FIG. 3 is a schematic diagram of ICD 14 according to one embodiment. The electronic circuitry enclosed within housing 15 includes software, firmware and hardware that cooperatively monitor one or more ECG signals, determine when a cardioversion-defibrillation shock is necessary, and deliver prescribed cardioversion-defibrillation therapies. In some examples, ICD 14 may be coupled to a lead, such as lead 16, carrying electrodes, such as electrodes 24, 28 and 30, positioned in operative relation to the patient's heart for delivering cardiac pacing pulses and may therefore include the capability to deliver low voltage pacing pulses as well as the high voltage shock pulses.

ICD 14 includes control module 80, associated memory 82, therapy delivery module 84, electrical sensing module 86, telemetry module 88, and cardiac signal analyzer 90. A power source 98 provides power to the circuitry of ICD 14, including each of the modules 80, 82, 84, 86, 88, and 90 as needed. Power source 98 may include one or more energy storage devices, such as one or more rechargeable or non-rechargeable batteries.

The functional blocks shown in FIG. 3 represent functionality that may be included in ICD 14 and may include any discrete and/or integrated electronic circuit components that implement analog and/or digital circuits capable of producing the functions attributed to ICD 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, processors, ASICs, memory devices, etc.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14. The non-transitory computer readable media storing the instructions may include any of the media listed above, with the sole exception being a transitory propagating signal.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, arrhythmia detection operations performed by cardiac signal analyzer 90 for determining a need for therapy delivered by ICD 14 may be implemented in control module 80 executing instructions stored in memory 82. As used herein, the term "module" refers to an application specific integrated circuit (ASIC), an electronic circuit, a processor (shared, dedicated, or group) and memory that execute one or more software or firmware programs, a combinational logic circuit, state machine, or other suitable components that provide the described functionality.

Control module 80 communicates with therapy delivery module 84, cardiac signal analyzer 90 and electrical sensing module 86 for sensing cardiac electrical activity, detecting cardiac rhythms, and generating cardiac therapies in response to sensed signals. Therapy delivery module 84 and electrical sensing module 86 are electrically coupled to electrodes 24, 28, and 30 carried by lead 16 (shown in FIG. 1) and housing electrode 15, which may serve as a common or ground electrode.

Electrical sensing module 86 is selectively coupled to electrodes 28, 30 and housing electrode 15 in order to monitor electrical activity of the patient's heart. Electrical sensing module 86 may additionally be selectively coupled to electrode 24. Sensing module 86 is enabled to selectively monitor one or more sensing vectors selected from the available electrodes 24, 28, 30 and 15. For example, sensing module 86 may include switching circuitry for selecting which of electrodes 24, 28, 30 and housing electrode 15 are coupled to sense amplifiers included in sensing module 86. Switching circuitry may include a switch array, switch matrix, multiplexer, or any other type of switching device suitable to selectively couple sense amplifiers to selected electrodes.

In some examples, electrical sensing module 86 includes multiple sensing channels for sensing multiple ECG sensing vectors selected from electrodes 24, 28, 30 and housing electrode 15. For example, a sensing vector between electrodes 28 and 30 may be selected for sensing a first ECG vector on one channel and at least one additional sensing vector may be selected between one of electrodes 24, 28 and 30 paired with the housing electrode 15 and received on another sensing channel. Each sensing channel may be configured to amplify and filter the ECG to improve the signal quality for sensing cardiac events, e.g., R-waves.

Each sensing channel of sensing module 86 includes a sense amplifier for receiving the ECG signals developed across the selected electrodes. The sense amplifiers pass sense event signals to control module 80 and/or cardiac signal analyzer 90. For example R-wave sense signals may be passed to tachyarrhythmia detector 94 and timing circuit 92 of cardiac signal analyzer 90 when a received ECG signal crosses a sensing threshold, which may be an auto-adjusting sensing threshold in some instances.

Sensing module 86 may include an analog-to-digital converter for providing a digital ECG signal to control module 80 and/or cardiac signal analyzer 90. In one example, two sensing channels are provided for receiving an ECG from a first sensing vector between electrodes 28 and 30 and a second sensing vector selected from either electrode 28 or electrode 30 paired with the housing electrode 15. The two ECG signals are converted to a multi-bit digital signal by sensing module 86 and provided to tachyarrhythmia detector 94 for performing ECG morphology analysis as described herein.

Cardiac signal analyzer 90 includes a tachyarrhythmia detector 94 for detecting and discriminating SVT, VT and VF and timing circuit 92. Timing circuit 92 may include various timers and/or counters for measuring time intervals, such as RR intervals, and setting time windows such as morphology template windows or morphology analysis windows relative to R-wave sense signals or for performing other timing related functions of cardiac signal analyzer 90.

The timing of R-wave sense signals received from sensing module 86 is used by timing circuit 94 to measure RR intervals. Tachyarrhythmia detector 94 may count RR intervals measured by timing circuit 92 that fall into different rate detection zones for determining a ventricular rate or performing other rate- or interval-based assessment for detecting ventricular tachyarrhythmia.

Tachyarrhythmia detector 94 receives digitized ECG signals from cardiac signal analyzer 90 for use in detecting tachyarrhythmia based on signal morphology. Examples of algorithms that may be performed by ICD 14 for detecting, discriminating and treating tachyarrhythmia and adapted to include techniques described herein are generally disclosed in U.S. Pat. No. 5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety.

The detection algorithm is highly sensitive and specific for the presence or absence of life threatening VT and VF. Therapy delivery module 84 includes a high voltage (HV) therapy delivery module including one or more HV output capacitors and, in some instances, a low voltage therapy delivery module. When a malignant tachycardia is detected the HV capacitors are charged to a pre-programmed voltage level by a HV charging circuit. Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the high voltage output circuit of therapy delivery module 84 to deliver high energy cardioversion/defibrillation shocks using defibrillation electrode 24 and housing electrode 15. Timing circuit 92 may be used to control R-wave synchronized shock pulses delivered by therapy delivery module 84.

It should be noted that implemented arrhythmia detection algorithms may utilize not only ECG signal analysis methods but may also utilize supplemental sensors 96, such as blood pressure, tissue oxygenation, respiration, patient activity, heart sounds, and the like, for contributing to a decision by control module 80 to apply or withhold a therapy.

Certain steps in the performance of the VT detection algorithm described herein are cooperatively performed in control module 80, including memory 82, cardiac signal analyzer 90 and stored detection criteria and other control parameters that may be programmed into memory 82 via telemetry module 88. Initial detection of VT or VF may be determined in the tachyarrhythmia detector 94 as a function of the time intervals between R-wave sense event signals that are output from sensing module 86. Discrimination of VT and SVT is performed by tachyarrhythmia detector 94 through analysis of the morphology of the sensed ECG signal(s) after an initial RR interval-based VT detection is made in some examples. Digital ECG signals received from one or more sensing channels of sensing module 86 may be stored in memory 82. Tachyarrhythmia detector 94 employs the digitized ECG signals stored in memory 82 in conjunction with morphology analysis.

As described below, digitized ECG signals are acquired during a stable heart rhythm (stable rate and morphology) and used by cardiac signal analyzer 90 to generate morphology templates for each available sensing vector, for example three vectors between electrodes 28 and 30, between electrode 28 and housing electrode 15, and between electrode 30 and housing electrode 15, respectively. A morphology template for each sensing vector is generated for multiple patient postures.

Morphology analysis performed by tachyarrhythmia detector 94 includes comparing one or more ECG signals sensed using selected sensing vectors during an unknown heart rhythm to morphology templates stored in memory 82 for the respective sensing vector. As indicated above, the unknown heart rhythm may be preliminarily detected as VT according to rate-based RR interval detection criteria using R-wave sense signals produced in response to one or more selected ECG signals. Some aspects of sensing and processing subcutaneous ECG signals are generally disclosed in commonly-assigned U.S. Pat. No. 7,904,153 (Greenhut, et al.), hereby incorporated herein by reference in its entirety.

A morphology template is generated for each available sensing vector for at least two different patient postures, for example sitting and lying. A morphology template may be an ensemble averaged waveform obtained from a predetermined number of cardiac cycles. A template window may be defined relative to R-wave sense signals produced by electrical sensing module 86. The ECG signal may be ensemble averaged across multiple template windows to obtain a waveform template for a given sensing vector and patient posture. Morphology templates may be updated periodically. Methods for generating and updating a morphology template and template comparisons performed by ICD 14 may include techniques generally disclosed in U.S. Pat. No. 6,745,068 (Koyrakh, et al.). U.S. Pat. No. 7,706,869 (Cao, et al.), and U.S. Pat. No. 8,428,697 (Zhang, et al.), all of which are incorporated herein by reference in their entirety.

A morphology analysis is performed by tachyarrhythmia detector 94 using the stored templates to determine whether morphology matching criteria is met based on a comparison between an ECG signal received by sensing module 86 during an unknown heart rhythm and a template generated by cardiac signal analyzer 90 during a known sinus rhythm and stored in memory 82. Numerous criteria may be used to determine the similarity or correlation between an ECG signal during an unknown rhythm and a template obtained during sinus rhythm. In one example, determining whether morphology matching criteria are met includes determining a morphology matching score or other metric of morphology similarity. An example of a morphology feature is a waveform area and a corresponding example of a morphology match metric may be a waveform area difference between the ECG signals received from the selected sensing vectors during an unknown cardiac rhythm and waveform areas stored for the selected sensing vectors. A normalized area waveform difference may be determined as generally disclosed in U.S. patent application Ser. No. 13/826,097, filed Mar. 14, 2013, (Zhang et al.), hereby incorporated herein by reference in its entirety. The morphology matching criteria may require the waveform area difference be within a predetermined percentage difference.

A wavelet transform method as generally disclosed in U.S. Pat. No. 6,393,316 (Gillberg et al.) is another example of a morphology matching method that may be implemented in the VT/SVT detection and discrimination techniques disclosed herein. Other morphology matching methods may be implemented by tachyarrhythmia detector 94 which compare the wave shape, amplitudes, slopes, inflection time points, number of peaks, or other features of the ECG signal, particularly of the R-wave or QRS portion of the ECG signal. As described herein, tachyarrhythmia detector 94 analyzes posture-dependent ECG templates for identifying posture-independent features of the templates. SVT discrimination features are selected from the posture-independent features for use by tachyarrhythmia detector 94 for discriminating VT from SVT.

The ECG morphology received across selected sensing vectors may vary with changes in patient posture. Comparison of the ECG morphology during an unknown fast rhythm to a morphology template obtained during sinus rhythm could result in a low morphology matching score due to a change in the ECG morphology caused by a change in patient posture. A fast rhythm that is sinus tachycardia could potentially be falsely detected as a shockable VT, leading to unnecessary shock therapy.

By obtaining multiple morphology templates generated for each available sensing vector for different patient postures, and identifying posture-independent features of those templates, those posture-independent features can be stored in memory 82 and compared to ECG signal features during an unknown rhythm in response to VT detection made by cardiac signal analyzer 90 based on cardiac intervals or other detection criteria. As described below, the digitized ECG signals received from sensing module 86 using selected sensing vectors during an unknown rhythm are compared to stored posture-independent template features without requiring the use of a posture sensor to determine the actual posture of the patient during the unknown rhythm. In other embodiments, sensors 96 may include a multi-dimensional accelerometer for detecting changes in patient posture for use in initially generating templates for different patient postures, from which the posture-independent features are extracted. A multi-axis accelerometer that may be used for detecting patient posture is generally disclosed in U.S. Pat. No. 5,593,431 (Sheldon), hereby incorporated herein by reference in its entirety.

Telemetry module 88 includes a transceiver and antenna for communicating with external device 40 (shown in FIG. 1) using RF communication. Under the control of control module 80, telemetry module 88 may receive downlink telemetry from and send uplink telemetry to external device 40. ECG episode data related to the detection of VT or VF and the delivery of a cardioversion or defibrillation shock may be stored in memory 82. Stored episode data is transmitted by telemetry module 88 to an external device 40 upon receipt of an interrogation command. Clinician review of episode data facilitates diagnosis and prognosis of the patient's cardiac state and therapy management decisions, including selecting programmable VT/VF detection and therapy delivery control parameters.

Figure 4:
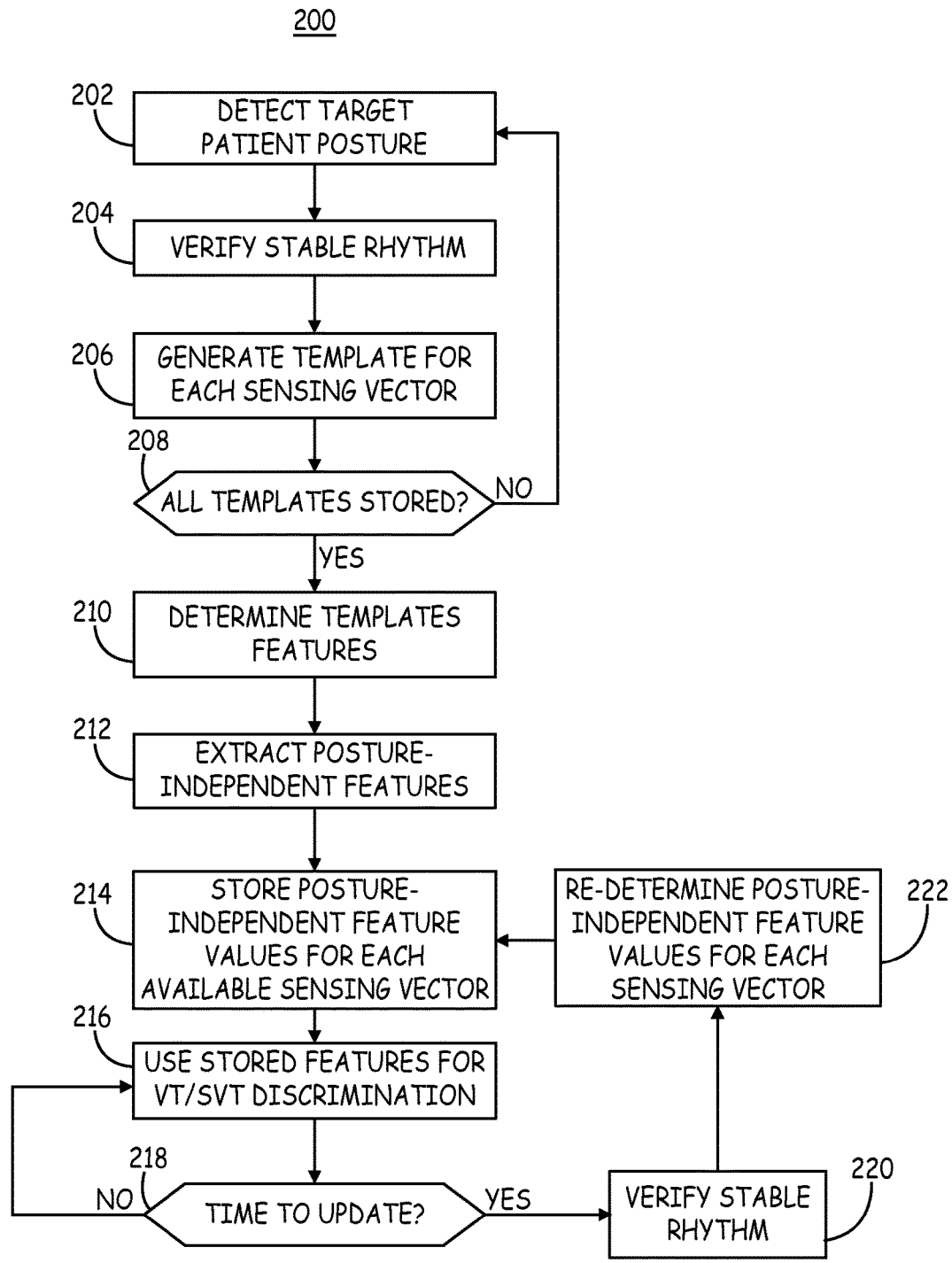
FIG. 4 is a flow chart of a method performed by an ICD for generating morphology templates and extracting posture-independent discrimination features for detecting and classifying VT and SVT.

FIG. 4 is a flow chart 200 of a method performed by ICD 14 for generating morphology templates and extracting posture-independent discrimination features for detecting and classifying VT and SVT. At block 202, a targeted patient posture is detected. An ECG morphology template is stored for multiple patient postures during a stable heart rhythm. In one example, an ECG template is generated for each of at least four patient postures including sitting (or standing but generally upright), supine, right-side lying, and left-side lying. Other postures may be used such as forward bending, reclined sitting, prone, etc. Any desired number and combination of postures may be used. The patient may be instructed to assume the first of the desired postures, either automatically by the external device display 54 (shown in FIG. 1) or by a clinician. A notification may be transmitted to the ICD 14 by user interaction with external device 40 to indicate that the patient has assumed one of the desired postures for generating a template. The ICD 14 detects that the patient is in a targeted posture for template generation in response to receiving the transmitted notification at block 202.

Alternatively, the ICD 14 may automatically detect a targeted patient posture using a posture sensor included in sensors 96 (FIG. 3). A posture sensor signal may be used by the ICD control module 80 to detect a change from a patient posture to a new posture. The control module 80 may determine if a template has been generated and stored in memory 82 for the new posture. If not, the control module 80 detects the new posture as a targeted posture at block 202 and initiates template generation by cardiac signal analyzer 90.

Prior to generating a template in response to detecting the targeted patient posture, the ICD 14 may first verify that the heart rhythm is stable at block 204 using one or more of the available sensing vectors. A stable heart rhythm may be a sinus rhythm or other supraventricular rhythm that is verified to have a stable heart rate over a required number of cardiac cycles and/or a stable ECG morphology over a required number of cardiac cycles. A stable rhythm may be normal sinus rhythm, sinus tachycardia, or an atrial paced rhythm when atrial pacing is available. In some examples, templates for each targeted posture may be generated at more than one sinus heart rate since changes in sinus heart rate can sometimes alter ECG morphology.

A morphology template may be generated at block 206 for each available sensing vector while the patient remains in the targeted posture. For example, the first posture may be a sitting position. The ICD 14 may generate a morphology template for a sensing vector between electrodes 28 and 30, a sensing vector between electrode 28 and the housing electrode 15, and a sensing vector between electrode 30 and the housing electrode 15 while the patient remains in the sitting position. The morphology template is stored for each of the three sensing vectors for the first posture. The ICD 14 may send a notification back to the external device 40 indicating that template generation is complete for a given posture so that the process of generating templates can proceed to the next posture.

The user may have the opportunity to reject a generated template if patient movement or other potential source of ECG noise artifact occurred during the template generation. In some examples, the ICD 14 may transmit generated templates to the programmer for display and acceptance by a clinician.

The patient may then be asked to assume a second posture, e.g., a supine position. The user may interact with external device 40 to transmit a notification that causes ICD 14 to detect the next patient posture based on the notification signal and begin ECG template generation for the second posture. The process of detecting that the patient has assumed a patient posture, based on a notification signal from the programmer, verifying a stable heart rhythm and generating a morphology template for each available sensing vector is repeated for a desired number of patient postures until templates for all postures have been obtained for each sensing vector. As indicated above, the ICD may detect different patient postures automatically and generate templates as new postures are detected until a complete set of templates for each of a desired number of postures for each available ECG sensing vector is generated.

The methods used to generate a template at block 206 may vary between examples. In one example, each template may represent a series of cardiac cycles that have been aligned over a template window and averaged to obtain an averaged cardiac cycle waveform that is stored as the template. A set of morphology templates is initially generated and stored for each available sensing vector for a desired number of different patient postures, for example at least two different postures such as sitting and lying. In one example, templates are generated for at least four different postures, e.g., any of sitting, standing, supine, prone, right-side lying, left-side lying, forward bending and reclined among others.

The actual patient posture is not necessarily stored with each morphology template and may even be unknown to ICD 14. The generated templates may be stored in ICD memory 82 with labels or numbering that corresponds to like postures across different sensing vectors. This labeling or numbering may be non-descriptive or non-identifying of what the actual patient posture was during generation of the templates. In other examples, the labeling or numbering may be descriptive or associated with the actual patient posture, e.g., based on a notification signal received from the external device 40 or based upon a posture sensor.

When a posture sensor is used for detecting a targeted patient posture for template generation, the actual patient posture, e.g., sitting, supine, prone, or side-lying, may or may not be determined. Detection of a change in posture may be adequate for triggering template generation. The generated templates may be labeled as Posture 1, Posture 2, Posture 3, etc. for each sensing vector such that templates generated for a common patient posture can be identified without necessarily knowing what the actual patient posture was.

Once a template is stored for each of a desired number of patient postures for each available sensing vector as determined at block 208, the templates generated for different postures for a given vector are compared to each other at blocks 210 and 212. The set of generated templates for each sensing vector represents the posture-dependency of the ECG morphology for a given sensing vector. This posture dependency may vary between sensing vectors and between patients. In some cases posture dependency may be high and in other cases posture dependency may be low or non-existent. The posture dependency of a given ECG sensing vector will be determined through the extraction and comparison of template features.

At block 210, various features of the templates are determined and compared to identify template morphology features that are substantially equal or the same between the posture-dependent templates for a given sensing vector. A set of template features is extracted from each template stored for each posture for each sensing vector. The set of features may include, without limitation, waveform area, Q-wave amplitude, Q-wave signal width, Q-wave slope, R-wave amplitude, R-wave signal width, R-wave slope, T-wave amplitude, T-wave slope, T-wave signal width, R-wave to Q-wave amplitude ratio, R-wave to T-wave amplitude ratio, R-T time interval, R-wave polarity, frequency content, number of peaks, time of maximum peak amplitude, time between maximum and minimum peaks, time of maximum positive slope, time of maximum negative slope, amplitude and/or polarity of peaks relative to a largest amplitude peak, timing of the centroid of the QRS complex, temporal pattern of a series of amplitude threshold crossings, temporal pattern of a series of slope threshold crossings, template wavelet coefficients generated using a wavelet transform, etc.

At block 212, analogous template features are compared across posture-dependent templates for a given sensing vector. Template features that are substantially equal between the posture-dependent templates are stored for a given sensing vector and referred to herein as "posture-independent features." These posture-independent features are extracted from the total set of template features at block 212 through a comparative analysis. For example an initial set of ten different template features may be determined from each posture-dependent template. Each of those ten template features are compared to the analogous template features determined from each of the other posture-dependent templates stored for the same sensing vector.

If a given template feature does not vary by more than a posture-independent threshold across templates for a given ECG sensing vector, that feature is identified as a posture-independent feature for that sensing vector. For example, if a given template feature does not vary by more than 10% or another predefined threshold for determining posture-independence between template features for the same sensing vector, that template feature is extracted as a posture-independent feature for that sensing vector at block 212. As another example, a feature extracted from multiple cardiac cycles during the same posture may be compared between cardiac cycles. The range or percentage variation of the feature between cardiac cycles for the same posture is determined as an intra-posture range or intra-posture percentage variation. An inter-posture range or inter-posture percentage variation of the given feature is also determined between posture-dependent templates. If the intra-posture range or percentage variation of the feature is approximately equal to the inter-posture range or percentage variation, the feature is posture-independent. To illustrate, a given feature may vary by approximately 5% between cardiac cycles during the same posture. The same feature may vary by approximately 5% between postures. Since the feature has the same inter-posture variability as the intra-posture variability, the feature is identified as a posture-independent feature.

The determination of whether a feature from one template is substantially equal to a feature from another template may include determining the respective features, determining a difference or ratio of the features, and comparing the difference or ratio of the features to a posture-independent threshold. Template sample point amplitudes may be normalized in some embodiments, e.g., by a maximum amplitude within a given template and features may be determined from normalized templates. A posture-independent threshold may be defined as a percentage, difference, range or other value based on the type of morphology feature being determined and compared.

At block 214, the posture-independent features extracted for each available sensing vector are stored. It is recognized that in some cases, available sensing vectors may have varying posture dependency. As such, a different set of posture-independent features may be extracted and stored for each available sensing vector. A set of posture-independent features for one sensing vector may have a different number of features and/or different types of features stored than the set of posture-independent features stored for another sensing vector.

In some examples, a minimum number of posture-independent features may be required for each sensing vector. If a sensing vector is not found to have at least the minimum number of posture independent features, that sensing vector may be excluded from the available sensing vectors that can be selected for morphology analysis during VT/SVT detection and discrimination. The excluded vector is determined to be highly posture dependent, which may lead to a false VT detection due to a low morphology match score caused by posture-induced changes in the ECG signal during a supraventricular rhythm.

Once a set of posture-independent features is stored for each available sensing vector, the stored feature sets are available for use in a VT/SVT detection and discrimination algorithm at block 216, as described below in conjunction with FIG. 5. The stored posture-independent feature sets are retrieved from memory 82 for use in the tachycardia discrimination algorithm performed by tachyarrhythmia detector 94.

Some or all of the process shown by flow chart 200 may be repeated periodically to update the stored posture-independent feature sets. For example, at block 218, the control module 80 may determine that it is time to update one or more posture-independent feature sets. The control module 80 may determine that it is time to update template feature values according to a scheduled basis, e.g., once a day, once a week, once a month, or other desired frequency.

The control module may additionally or alternatively determine that it is time to update stored feature values in response to comparing the feature values to analogous ECG features during a stable, supraventricular rhythm. For example, once a day or on another scheduled basis, the stored feature values may be compared to the ECG signal for a respective sensing vector for one or more cardiac cycles. Since the features are posture-independent, the posture of the patient during the comparisons need not be determined. If the ECG signal during the stable supraventricular rhythm still matches the stored features for the same sensing vector within predetermined update criteria, the features are not updated. The tachyarrhythmia detector 94 continues to use the presently stored features at block 216. If the ECG signal during the stable supraventricular rhythm does not match the stored posture-independent template feature values based on predetermined update criteria, the control module 80 determines that it is time for an update.

If the control module 80 determines that it is time to update stored template features at block 218, the cardiac signal analyzer 90 verifies that the cardiac rhythm is a stable, supraventricular rhythm at block 220. At block 222, new values for stored template features are re-determined for one or all available sensing vectors, without determining the patient's posture since the features have already been identified as being posture-independent. The re-determined values are stored for each posture-independent feature for each sensing vector at block 224. It is recognized that not all available sensing vectors may require updates at the same time and that updated features may be stored for some of the available sensing vectors at block 224 but not all available sensing vectors during each update.

Periodic updates at block 222 may include obtaining new values for posture-independent template features stored for a given sensing vector without re-determining which template features are posture-independent for that sensing vector. It may be assumed that the features that are first identified at block 212 as being posture-independent for a given sensing vector will remain independent. Only the values of the posture-independent features need updating.

In other cases, the feature set may be periodically re-evaluated for posture-independency. Accordingly, in some examples, the process shown by FIG. 4 may be repeated beginning at step 202 for updating the set of posture-independent template features that is stored for a given sensing vector. Templates may be generated at block 206 for each sensing vector to be updated for multiple patient postures as described above. The variation or range of previously identified posture-independent features may be re-determined from the newly generated templates at block 210 to verify that each feature remains posture-independent without requiring determining and comparing a larger number of template features. Alternatively, a larger set of posture-independent features is determined at block 210 a described above, from which a new set of posture-independent template features is extracted at block 212. The members of the posture-independent feature set may change over time in some cases.

Figure 5:
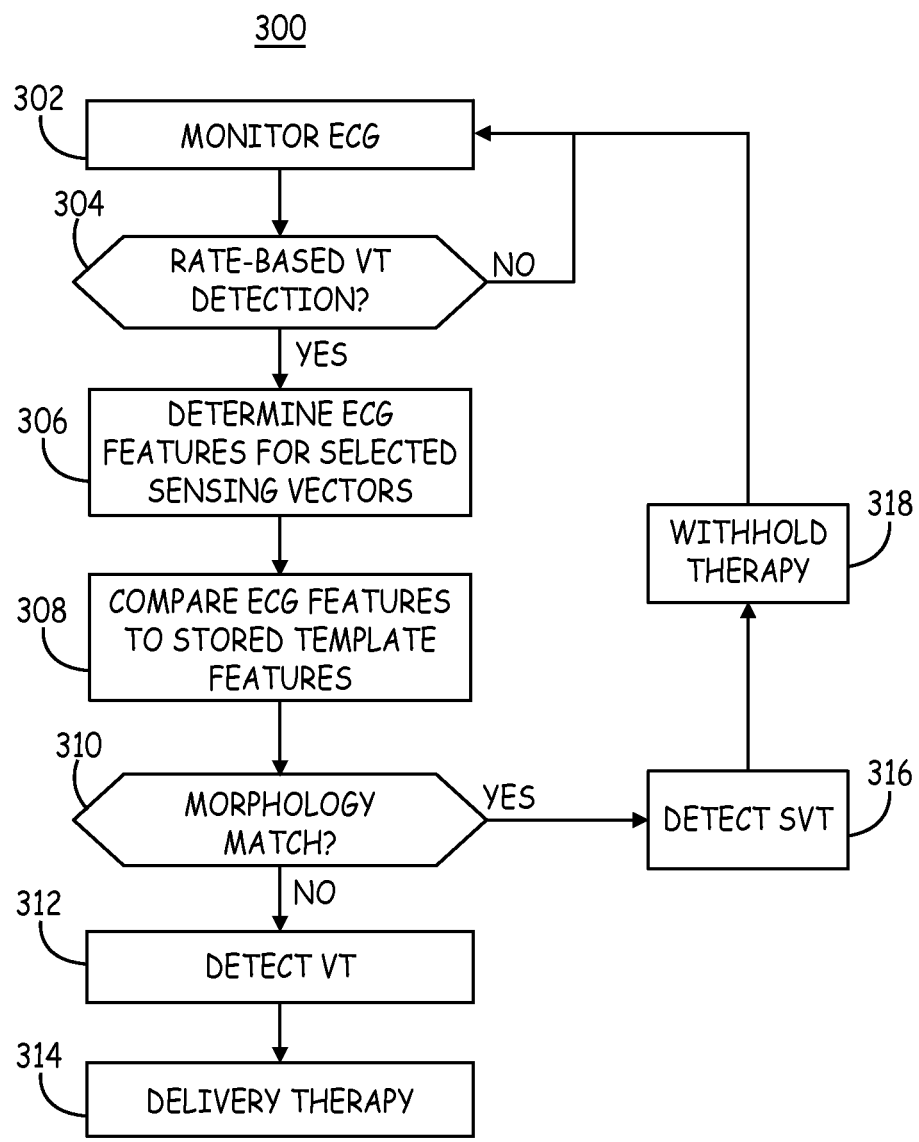
FIG. 5 is a flow chart of a method for discriminating between VT and SVT according to one example.

FIG. 5 is a flow chart 300 of a method for discriminating between VT and SVT according to one example. At block 302, an ECG signal is received across one or more selected sensing vectors. Referring to the example of FIG. 1, ECG1 may be an ECG signal received across the vector between sensing electrodes 28 and 30. ECG2 may be an ECG signal received across the vector between electrode 28 and the housing electrode 15, and ECG3 may be an ECG signal received across electrodes 30 and the housing electrode 15. ICD 14 may be configured with at least two sensing channels and may select two out of three available sensing vectors, such as two out of ECG1, ECG2 and ECG3. In other examples, one or more ECG sensing vectors may be selected from one or more available sensing vectors.

In some examples, VT is initially detected based on heart rate. R-wave sense signals are produced by the ICD sensing module in response to R-wave sensing threshold crossings of at least one or all selected ECG signals. RR intervals are determined by the cardiac signal analyzer 90 in response to R-wave sense signals. RR intervals are used at block 304 to detect VT according to rate or interval-based VT detection criteria. For example, VT may be detected based on a required number of intervals to detect (NID) falling into a programmed VT interval range. To illustrate, a VT detection interval range may include RR intervals less than or equal to 360 ms and greater than 320 ms. A ventricular fibrillation detection interval (FDI) range may be defined as RR intervals less than or equal to 320 ms. The VT NID may be set to 12 consecutive intervals, 24 consecutive intervals or another required number of VT detection intervals. If the required number of consecutive RR intervals are in the VT detection interval range, a preliminary VT detection may be made.

In other examples, primary VT detection criteria may include a prioritized set of inter-related rules pertaining to cardiac intervals, interval patterns and or morphology; rate onset; stability; and/or gross morphology detection criteria or any combination thereof. Various examples of VT detection criteria that may be used as primary detection criteria at block 304 are disclosed in the above-incorporated patents, such as U.S. Pat. No. 5,545,186 (Olson, et al.), U.S. Pat. No. 7,031,771 (Brown, et al.), U.S. Pat. No. 8,160,684 (Ghanem, et al.), and U.S. Pat. No. 8,437,842 (Zhang, et al.).

If VT detection is made based on RR intervals or other primary detection criteria, at block 304, a comparative morphology analysis of the unknown rhythm with posture-independent template features is performed at blocks 306 through 310 before confirming a VT rhythm classification and delivering a VT therapy. The morphology analysis is performed to determine if the morphology of the received ECG signal(s) during the unknown rhythm matches posture-independent template features stored for the corresponding ECG sensing vector(s).

In order to make this comparison, the cardiac signal analyzer determines which posture-independent features have been stored for a given sensing vector. Those features are then determined from the ECG signal at block 306 during the unknown rhythm, which has been preliminarily detected as VT based on RR interval or other primary detection criteria. The features may be determined from single cardiac cycles over one or more beats for performing beat-by-beat feature comparisons. Alternatively, one or more cardiac cycles during the unknown rhythm may be aligned within a morphology analysis window and ensemble averaged. The ECG features are then determined from the averaged cardiac cycle at block 308.

If more than one ECG signal is being monitored, the posture-independent features that have been stored for each sensing vector are determined from each respective ECG signal. The actual patient posture need not be determined since the features being determined have been identified as posture-independent features.

At block 308, the features determined from the ECG signal(s) during the unknown rhythm are compared to the stored, posture-independent template features for each respective sensing vector. If features have been extracted from single cardiac cycles of the ECG signal during the unknown rhythm, a beat-by-beat comparison may be made. In one example, if a feature of at least n out of m beats, for example 3 out of 5 beats, match the analogous posture-independent template feature, that feature is determined to match the template feature. Alternatively, the features extracted from the ensemble averaged signal during the unknown cardiac rhythm are compared to the analogous posture-independent template features. The comparison between individual beat features or an ensemble averaged cardiac cycle signal to determine a similarity between the unknown cardiac rhythm and the stored template features may involve determining a morphology match metric for each feature as a percentage, sign change, numerical difference, ratio, or other comparative parameter for each posture-independent feature.

The morphology match metric of a given feature during the unknown rhythm may be determined as the difference between the feature and the template feature expressed as a percentage of the stored template feature. For example, an R-wave width metric may be determined as ((1−R-wave width difference)/template R-wave width)*100, where R-wave width difference is the absolute difference between the R-wave width of an unknown individual beat or averaged cardiac cycle and the template R-wave width. If the R-wave width metric is at least 90%, the R-wave width of the cardiac signal during the unknown rhythm and the R-wave width template feature match.

In another example, a normalized waveform area difference (NWAD) may be determined as ((1−AD)/TEMPLATE WA)*100 where AD is the absolute area difference between the normalized ECG signal waveform during an unknown rhythm and the normalized template waveform. TEMPLATE WA (waveform area) is the area of the normalized template waveform. The waveforms may be normalized by a maximum sample point amplitude of the waveform. If the NWAD is at least 90% (or other threshold percentage), the WA of the unknown signal matches the WA of the template.

Once a morphology match metric for each posture-independent feature for each ECG sensing vector has been determined, overall morphology match criteria are applied at block 310 to the morphology match metrics. In some examples, each ECG vector signal during the unknown rhythm is first classified as SVT or VT based on the morphology match metrics determined for each posture-independent feature for that sensing vector. Each morphology match metric may be compared to a match threshold to determine if an individual morphology match metric of an individual ECG feature matches the posture-independent feature. Actual values defined as the morphology match thresholds applied to different posture-independent feature comparisons may vary between embodiments and will be based on the type of signal feature being compared. Different morphology match criteria may be applied to different posture-independent features. For example some features may be required to match a posture-independent template feature more closely than other features.

An ECG vector signal during the unknown rhythm may be classified as SVT if a required number of the ECG signal features during the unknown rhythm match the posture-independent template features for that sensing vector based on a morphology match criteria for each respective feature. Morphology match criteria applied to a single vector may require at least one feature be within a predetermined range or percentage, e.g., 10% or other predetermined percentage threshold, of the analogous posture-independent template feature. To illustrate, if one of the stored posture-independent features is QRS signal width, and the template QRS signal width is 120 ms, the ECG signal during the unknown rhythm may be required to be within 10 ms or 10% of the template QRS signal width.

If n posture-independent template features have been stored for a given sensing vector, at least one of the n posture-independent template features may be required to match the analogous ECG signal feature during the unknown rhythm based on matching criteria for the respective features in order to classify that sensing vector as SVT. In another example, a majority of the stored posture-independent template features, e.g. two out of three stored posture-independent template features, may be required to match analogous ECG signal features within respective matching criteria in order to classify the sensing vector signal as SVT. In some cases, all features determined from one sensing vector may be required to match all analogous posture-independent template features within respective matching criteria for that sensing vector in order to classify that sensing vector signal as SVT during the unknown rhythm. If no ECG signal features, or less than a threshold number of ECG signal features, match the analogous posture-independent template features based on matching criteria defined for each feature or defined for a combination of features, the sensing vector is classified as VT.

Once each sensing vector is classified as SVT or VT, an overall SVT or VT detection is made at block 316 or block 312. In one example, SVT detection criteria require that at least one sensing vector yields an SVT classification at block 316. Morphology match criteria applied at block 310 are also referred to herein as "SVT detection criteria" since a match would indicate that the rhythm is supraventricular in origin.

In other examples, SVT detection criteria applied at block 310 may include different logical combinations of the morphology matching results determined for features from multiple ECG vectors without classifying the individual ECG sensing vectors during the unknown rhythm. For example, if at least one signal feature from one sensing vector matches a respective posture-independent template feature, and at least one ECG signal feature from another sensing vector matches a respective posture-independent template feature, or if at least two ECG signal features from the same sensing vector match respective posture-independent template features, SVT may be detected at block 316. In other words, if the ECG signal from each sensing vector matches a first threshold number of template features, e.g., one each, or if the ECG signal of only sensing vector matches a second, higher threshold number of template features, e.g., at least two, SVT is detected. In an example where three posture-independent features are stored for each of two sensing vectors, this decision step may be stated logically as:

IF one of ECG1 features 1, 2, or 3 match AND one of ECG2 features 1, 2 or 3 match,
THEN SVT;
OR
IF two of ECG1 features 1, 2, and 3 match OR two of ECG2 features 1, 2, and 3 match,
THEN SVT;
ELSE VT.

It is recognized that numerous SVT detection criteria may be conceived that are based on different combinations of posture-independent feature comparisons from one or more ECG sensing vectors.

If SVT is detected at block 316, VT therapy is not delivered. In particular, a shock therapy is withheld as indicated at block 318 since the SVT is deemed a non-treatable rhythm. ECG monitoring continues by returning to block 302. If the SVT detection criteria are not satisfied at block 310, the primary VT detection made at block 304 is confirmed at block 312. The ICD 14 delivers a therapy to treat the VT at block 314. A cardioversion/defibrillation shock may be delivered. In IMD systems that include pacing capabilities, ATP may be delivered prior to delivering a shock therapy.

The SVT detection criteria applied at block 310 based on posture-independent feature comparisons are described as being secondary VT/SVT detection criteria that are applied only after a preliminary VT detection has been made based on primary VT detection criteria, such as RR interval-based criteria. In other examples, the morphology match criteria applied to comparisons between an ECG signal during an unknown rhythm with posture-independent template features may be the primary VT detection criteria, used with or without other primary and/or secondary detection criteria.

Figure 6:
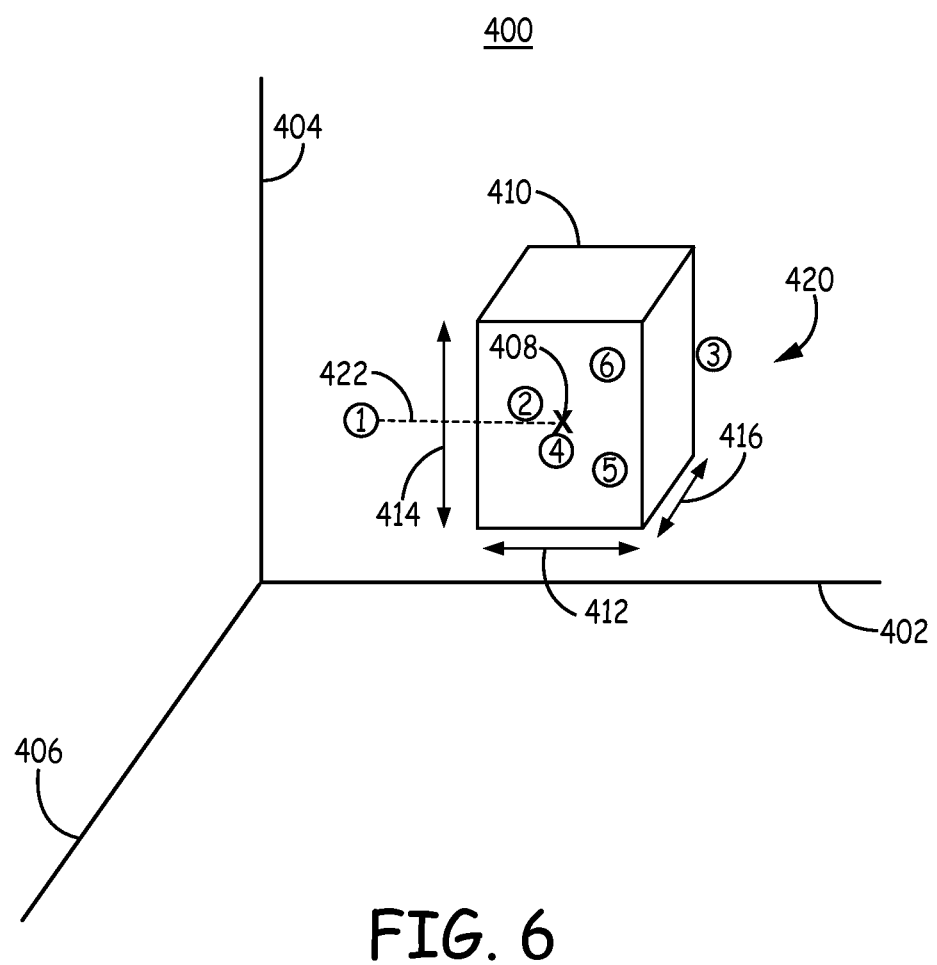
FIG. 6 is a multi-dimensional plot of posture-independent features depicting an SVT classification region.

FIG. 6 is a multi-dimensional plot 400 of posture-independent features depicting an SVT classification region 410. Plot 400 depicts an alternative method that may be performed by cardiac signal analyzer 90 for classifying an ECG sensing vector as SVT or VT during an unknown cardiac rhythm. In an illustrative example, multiple features may be extracted from each posture-dependent template for a given ECG sensing vector, for example eight, ten or more features of the posture-dependent template. After comparing the features, a set of posture-independent features for the sensing vector is identified. This process corresponds to the flow chart 200 shown in FIG. 4. The resulting set of posture-independent features may vary in the number of features identified as being posture-independent. In the example shown in FIG. 6, a set of three features are identified as posture independent features for the given ECG sensing vector. These three features can be visualized in a three-dimensional plot 400, with Feature 1 plotted along an x-axis 402, Feature 2 plotted along a y-axis 404 and Feature 3 plotted along a z-axis 406.

The point "X" 408 indicates the location of the template values of three posture-independent features, Feature 1, Feature 2 and Feature 3, determined as x-, y- and z-coordinates in the three-dimensional space of plot 400 for a given sensing vector. For example, Feature 1 may be R-wave width, Feature 2 may be Q-wave width, and Feature 3 may be the time of maximum positive R-wave slope. It is recognized that a plot of posture-independent features for a given ECG sensing vector may be 1-dimensional, 2-dimensional, 3-dimensional or any n-dimensional plot where "n" is the number of posture-independent features identified for the given ECG sensing vector.

The SVT classification region 410 is defined by a morphology match threshold range 412, 414, and 416 for each respective Feature 1, Feature 2, and Feature 3. The morphology match threshold ranges may represent a range of values for a given feature that is within ±5%, ±10% or other acceptable range of the template feature value. Six individual cardiac cycles during an unknown rhythm are represented by points 1-6 420 (circle symbols). The cardiac cycles 1 through 6 during the unknown rhythm have been analyzed beat-by-beat to determine the values of Feature 1, Feature 2, and Feature 3 for each cycle. The cardiac cycle feature values are represented by each of the plotted cardiac cycle points 1-6 420. In other words, the features of each cardiac cycle are represented by the x-, y- and z-coordinates of points 1-6 420 in the three dimensional space.

Cardiac cycles 2, 4, 5 and 6 fall within the SVT classification region 410 and represent cardiac cycles having morphology features matching the three analogous posture-independent template features based on morphology match threshold ranges 412, 414, and 416. Cardiac cycles 2, 4, 5 and 6 are classified as SVT cycles. Cardiac cycles 1 and 3 fall outside the SVT classification region 410 and represent cardiac cycles that do not match the posture-independent template features. Cardiac cycles 1 and 3 are classified as VT cycles. In one example, if n of m cycles are classified as SVT points because they fall within the SVT classification region 410, e.g., if four out of six cardiac cycle points fall within the SVT classification region 410 as shown, the ECG signal for the sensing vector being analyzed is classified as SVT. If less than n of m cardiac cycles fall within the SVT classification region 410, the ECG sensing vector is classified as VT. In other examples, an ECG sensing vector is classified as VT if at least a threshold number of consecutive cardiac cycles are classified as VT, i.e., all cardiac cycle points fall outside SVT classification region 410. In some instances, 12, 24 or another number of consecutive cardiac cycle points may be required to fall outside the SVT classification region 410 in order to classify the ECG sensing vector signal during the unknown rhythm as a VT signal.

If only one ECG sensing vector is being used, the unknown rhythm is detected as SVT or VT based on the SVT or VT classification of that sensing vector. If more than one ECG sensing vector is being used, SVT is detected if at least one sensing vector is classified as SVT during the unknown rhythm.

In other examples, an ensemble averaged cardiac cycle during the unknown rhythm is compared to the posture-independent template features. In this case, a single point, e.g., Point 1 may be determined as having x-, y-, z-coordinates set equal to the values determined from the averaged cardiac cycle for each respective Feature 1, Feature 2 and Feature 3. If Point 1 falls outside the SVT classification region 410 as shown, the ECG sensing vector signal is classified as VT during the unknown rhythm. If a single point representing the posture-independent features of an averaged cardiac cycle falls within the SVT classification region 410, the ECG sensing vector signal is classified as SVT during the unknown rhythm.

The cubic shape of the SVT classification region 410 depicted in FIG. 6 is a case where the acceptable values of the posture-independent features are independent of each other. It is also recognized that the shape of the SVT classification region 410 of FIG. 6 can take a form where the acceptable values of the features are interdependent resulting in a sphere, ellipsoid, or other shape, and is not constrained to 3 dimensions based on three posture-independent features.

In some cases, a morphology match threshold applied to a set of features determined from an ECG signal during an unknown rhythm may be defined as a maximum distance from the template point 408 in the n-dimensional space of plot 400. The distance 422 in the n-dimensional space between Point 1 for the unknown cardiac signal and the template point 408 may be determined based on mathematical relationships. The distance 422 is compared to a morphology match distance threshold. If the distance 422 is greater than a morphology match threshold, Point 1 is classified as a VT point. If the distance 422 is less than the morphology match threshold, the point is classified as an SVT point. If the point represents an ensemble average of multiple cardiac cycles of the unknown rhythm, the ECG sensing vector signal is classified according to the classification of the point. Alternatively, if multiple points are classified in a beat-by-beat analysis, the ECG sensing vector signal is classified based on a required number of points being within (or more than) a morphology match distance threshold. For example, if a threshold number of consecutively determined points are more than the threshold distance from the template feature point 408, the sensing vector is classified as VT. A final VT or SVT detection is based on the classifications of one or more ECG sensing vector signals during the unknown rhythm.

Figure 7:
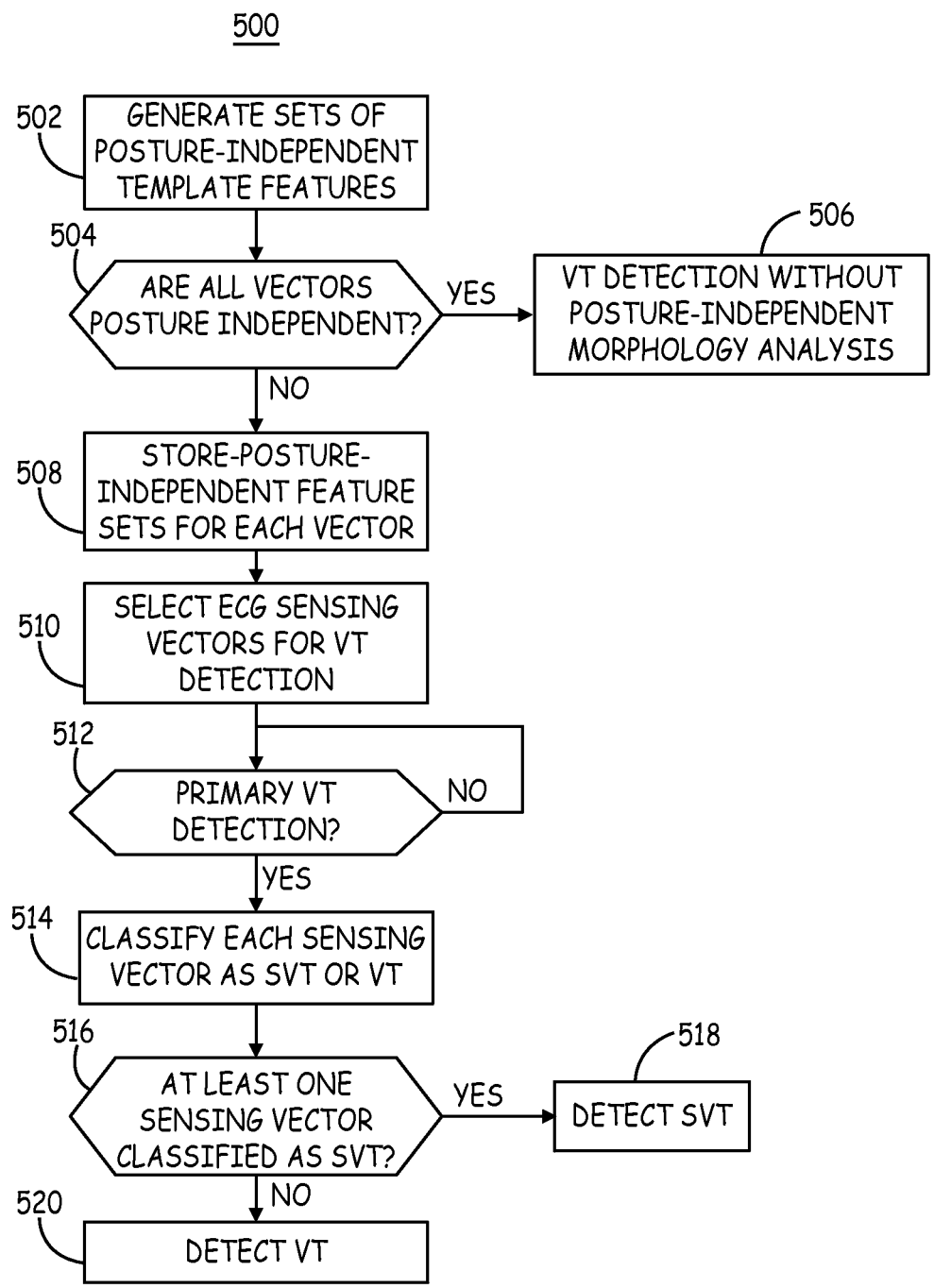
FIG. 7 is a flow chart of a method for performing VT detection according to another example.

FIG. 7 is a flow chart 500 of a method for performing VT detection according to another example. At block 502, a set of posture-independent template features is generated for each available sensing vector, e.g., as described in conjunction with FIG. 4. In some patients, ECG signals may be posture-independent and in other patients, changes in posture alter the ECG signals. In patients presenting posture-independency, the set of template features determined for one posture matches the set of template features for all postures for a given sensing vector. If all ECG sensing vectors are posture independent, as determined at block 504, the cardiac signal analyzer 90 may perform VT detection without performing a comparison of ECG signal features to posture-independent template features, as indicated at block 506. For example, any interval and/or morphology based detection criteria may be used without determining posture-independent features of the ECG signal or comparing those features to stored posture-independent template features.

If all vectors are not posture independent (block 504), the posture-independent features sets are stored for each of the sensing vectors at block 508. The VT detection algorithm performed by ICD 14 will include comparisons to posture-independent template features (for at least some ECG sensing vectors).

At block 510, ECG sensing vectors are selected for VT detection. One or more vectors may be selected. Vector selection may be based at least in part on the posture dependency of each available vector. In some cases, a single vector may be highly posture dependent such that all features or a majority of features are posture dependent (none or a small minority of the template features are stored as posture-independent features). Other vectors may be relatively less posture dependent with a relatively larger number of posture-independent features stored. Vector selection at block 510 may therefore include selecting one or more vectors that present the highest posture independency based on the number of posture-independent features stored. Vectors having a higher number of posture-independent features may be selected before vectors having a lower number of posture-independent features stored. All or a subset of the posture-independent features stored may actually be used for comparison to ECG signal features during an unknown rhythm. Posture-independency may be one criterion used for ECG sensing vector selection among other selection criteria, such as signal-to-noise ratio or other signal quality parameter requirements.

At block 512, VT is detected based on primary detection criteria, e.g., based on RR intervals, RR interval stability, rate onset, and/or gross morphology. In some cases, the ECG signal(s) used for primary VT detection at block 512 may be the same or different than the ECG signal(s) selected at block 510 for posture-independent template feature comparisons.

In response to a preliminary VT detection, ECG signal features are determined from each sensing vector selected at block 510 that are analogous to the stored posture-independent template features for the respective sensing vector. As indicated above, all or a subset of stored posture-independent template features may be used. Based on a comparative analysis of the ECG signal features and the corresponding posture-independent template features, e.g., as described in conjunction with FIG. 5 or 6, each selected ECG signal vector is classified as an SVT or VT rhythm at block 514.

If at least one ECG sensing vector is classified as SVT, as determined at block 516, the unknown rhythm is detected as SVT at block 518. In another example, SVT detection criteria may require that all selected ECG sensing vectors are classified as SVT. If none of the selected ECG sensing vectors are classified as SVT, the primary VT detection at block 512 is confirmed at block 520.

Thus, a method and apparatus for detecting and discriminating VT and SVT have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. A method performed by an implantable medical device, comprising:
    sensing a first cardiac signal during a known cardiac rhythm from each of a plurality of available sensing vectors,
    for each of the plurality of available sensing vectors, generating a plurality of morphology templates of the first cardiac signal for each of a plurality of patient postures;
    determining a set of template features from each of the plurality of morphology templates;
    for each of the plurality of available sensing vectors, comparing the set of template features from one of the plurality of morphology templates corresponding to one of the plurality of postures to each of the sets of template features from all of the other morphology templates corresponding to all of the other of the plurality of postures;
    for each of the plurality of available sensing vectors, storing a set of posture-independent template features in response to the comparing;
    sensing a second cardiac signal during an unknown cardiac rhythm from at least one of the plurality of available sensing vectors;
    determining features from the second cardiac signal that are analogous to the set of posture-independent template features stored for the at least one of the plurality of available sensing vectors;
    comparing the features determined from the second cardiac signal to the analogous set of posture-independent template features; and
    classifying the unknown cardiac rhythm in response to comparing the features determined from the second cardiac signal to the analogous set of posture-independent template features.

2. The method of claim 1, wherein classifying the unknown cardiac rhythm comprises:
    selecting at least two of the available sensing vectors;
    classifying each of the at least two of the available sensing vectors as one of ventricular tachycardia and supraventricular tachycardia in response to the comparing the features determined from the second cardiac signal to the set of posture-independent templates for the respective sensing vector; and
    classifying the unknown cardiac rhythm as supraventricular tachycardia in response to at least one of the selected sensing vectors being classified as supraventricular tachycardia.

3. The method of claim 1, further comprising:
    producing a supraventricular tachycardia classification region of an n-dimensional space defined by the set of posture-independent features for a respective one of the available sensing vectors;
    wherein comparing the features determined from the cardiac signal to the set of posture-independent templates comprises determining if the features define a point within the supraventricular tachycardia classification region.

4. The method of claim 1, further comprising:
    determining each set of posture-independent features as a posture-independent set of coordinates in an n-dimensional space, the set of coordinates comprising a value of each posture-independent feature included in a respective set of posture-independent features, wherein the n-dimensional space comprises a dimension corresponding to each posture-independent feature included in the set of posture-independent features;
    determining the features from the second cardiac signal as a cardiac signal set of coordinates in the n-dimensional space;
    determining a distance between the cardiac signal set of coordinates and the posture-independent set of coordinates; and
    classifying the unknown cardiac rhythm based on the determined distance.

5. The method of claim 4, further comprising comparing the distance to a supraventricular tachycardia classification threshold and classifying the unknown cardiac rhythm as supraventricular tachycardia in response to the distance being less than the threshold.

6. The method of claim 1, further comprising:
    determining features from each one of a plurality of cardiac cycles from the second cardiac signal that are analogous to the set of posture-independent template features stored for the at least one of the plurality of available sensing vectors;
    comparing the features determined from each one of the plurality of cardiac cycles to the analogous set of posture-independent template features; and
    classifying the at least one of the plurality of available sensing vectors in response to a threshold number of the plurality of cardiac cycles matching the analogous set of posture-independent template features; and
    classifying the unknown cardiac rhythm based on the classification of the at least one of the plurality of available sensing vectors.

7. The method of claim 1, wherein determining the features of the second cardiac signal comprises:

determining an average cardiac cycle signal from a plurality of cardiac cycles of the cardiac signal; and determining the features of the second cardiac signal from the averaged cardiac cycle.

8. The method of claim 1, wherein the classifying comprises classifying the unknown cardiac rhythm as one of supraventricular tachycardia and ventricular tachycardia.

9. The method of claim 8, further comprising classifying the unknown cardiac rhythm as a supraventricular tachycardia in response to at least one feature of the second cardiac signal matching an analogous feature of the set of posture-independent features within a predetermined match threshold.

10. The method of claim 8, further comprising withholding a ventricular tachycardia therapy in response to classifying the unknown cardiac rhythm as a supraventricular tachycardia.

\* \* \* \* \*